United States Patent [19]

Schwieker et al.

[11] Patent Number: 4,577,341
[45] Date of Patent: Mar. 18, 1986

[54] DIAPHRAGM ARRANGEMENT FOR X-RAY SPOT-FILM DEVICE

[75] Inventors: Horst H. Schwieker; Kurt Gieschen, both of Hamburg, Fed. Rep. of Germany

[73] Assignee: U.S. Philips Corporation, New York, N.Y.

[21] Appl. No.: 471,931

[22] Filed: Mar. 3, 1983

[30] Foreign Application Priority Data

Mar. 17, 1982 [DE] Fed. Rep. of Germany ....... 3209683

[51] Int. Cl.⁴ .......................... G21K 1/02; G21K 1/04
[52] U.S. Cl. .................... 378/150; 378/152; 378/176
[58] Field of Search ............... 378/160, 161, 175, 176, 378/147–159; 354/229, 230, 125

[56] References Cited

U.S. PATENT DOCUMENTS

| 3,875,411 | 4/1975 | Kunert | 250/402 |
| 3,975,642 | 8/1976 | Kunert | 378/160 |
| 4,058,817 | 11/1977 | Johnson | 354/230 |
| 4,221,971 | 9/1980 | Burger | 250/505 |
| 4,335,945 | 6/1982 | Johnson | 354/230 |
| 4,352,987 | 10/1982 | Hayashi | 378/150 |
| 4,380,819 | 4/1983 | Everett | 378/175 |
| 4,490,835 | 12/1984 | Wons | 378/147 |

FOREIGN PATENT DOCUMENTS 1441312 10/1968 Fed. Rep. of Germany .
2842659 4/1980 Fed. Rep. of Germany ...... 378/150

Primary Examiner—Craig E. Church
Assistant Examiner—Charles F. Wieland
Attorney, Agent, or Firm—Marc D. Schechter

[57] ABSTRACT

The invention relates to diaphragm means arranged close to the film in an X-ray spot film device. The diaphragm means comprises a first diaphragm with several rectangular aperture sections. The sections are displaced in the horizontal direction and have different vertical dimensions. A second diaphragm assembly has vertically extending diaphragm edges. By moving the first diaphragm to different positions in the radiation path, the aperture can be adapted to exposure formats of different vertical dimensions.

11 Claims, 2 Drawing Figures

DIAPHRAGM ARRANGEMENT FOR X-RAY SPOT-FILM DEVICE

BACKGROUND OF THE INVENTION

The invention relates to X-ray spot-film devices having diaphragms which are arranged close to the film. One diaphragm in each device has horizontal diaphragm edges extending symmetrically with respect to a horizontal center line. Another diaphragm has vertically extending diaphragm edges.

Such a spot-film device is described in German Offenlegungsschrift No. 2842659. The terms "horizontal" and "vertical" relate to the spot-film device in a standing position, with the two diaphragm assemblies extending in vertical planes. The term "center line" designates a horizontal or vertical straight line passing through the center of the exposure or radiographic field struck by radiation.

In FIG. 4 of the known device, one diaphragm comprises a U-shaped diaphragm plate, and the other diaphragm comprises a rectangular diaphragm plate. In order to limit the width of the exposure field, the two diaphragm plates are moved toward each other so that the exposure field remains between the vertical edges facing each other. In order to limit the height and width of the exposure field, the two diaphragm plates are displaced along each other so that the exposure field is limited by the horizontally arranged U of the first diaphragm plate and by one vertical diaphragm edge of the second diaphragm plate.

A disadvantage of the known X-ray spot-film device is that when limiting the width of the exposure field, the exposure field has a predetermined height. Moreover, the control of each of the two diaphragm plates depends both upon the height and width of the exposure field. and the Furthermore, spot-film devices are known, in which the width of the exposure field is determined by two diaphragm plates which are coupled to each other so that their vertical edges facing each other invariably extend symmetrically about the vertical center line. For exposures, in which the height of the exposure should be limited, exchangeable plates or compression chambers can be arranged in the radiation path. However, exchanging plates has a disturbing effect during the examination and is not practicable in various kinds of examination.

SUMMARY OF THE INVENTION

It is an object of the invention to provide an X-ray spot-film device which can easily be adapted to various exposure formats.

According to the invention, this is achieved in that the height-limiting diaphragm comprises several rectangular sections relatively displaced horizontally. The apertures extend symmetrically with respect to the horizontal center line and having relatively different vertical dimensions.

According to the invention, the height-limiting diaphragm is moved into the radiation path over such a distance that that section of the diaphragm in the radiation path determines the vertical dimensions of the exposure field The edges of this section of the diaphragm have a relative distance corresponding to the desired height.

Essentially, the width of the diaphragm aperture could then, as in the German Offenlegungsschrift No. 2842659, be determined by the position of this height-limiting diaphragm in combination with the width-limiting diaphragm assembly taking the form of a diaphragm plate with vertical edges. However, especially with two or more sections, it would then be necessary to provide a wide vertical strap between the individual sections of the height-limiting diaphragm plate, so that the horizontal dimensions of such a plate would be very large. Moreover, the positions of the two diaphragm plates would have to be controlled in a complicated manner, depending upon the width and the height of the diaphragm apertures.

According to a further embodiment of the invention, the width-limiting diaphragm assembly therefore comprises two diaphragm plates. The two plates are coupled to each other so that their vertical edges facing each other invariably extend symmetrically with respect to the vertical center line. The width of the diaphragm aperture is then determined by the distance between the facing diaphragm edges of the two diaphragm plates of the width-limiting diaphragm assembly. Consequently, no vertical straps are required between the sections of the height-limiting diaphragm plate. The position of the height-limiting diaphragm determines the height of the diaphragm aperture, and the positions of the two diaphragm plates of the width-limiting diaphragm assembly determine its width.

BRIEF DESCRIPTION OF THE DRAWING

The invention will now be described more fully with reference to the accompanying drawing, in which.

DESCRIPTION OF THE PREFERRED EMBODIMENTS

Figure 1:
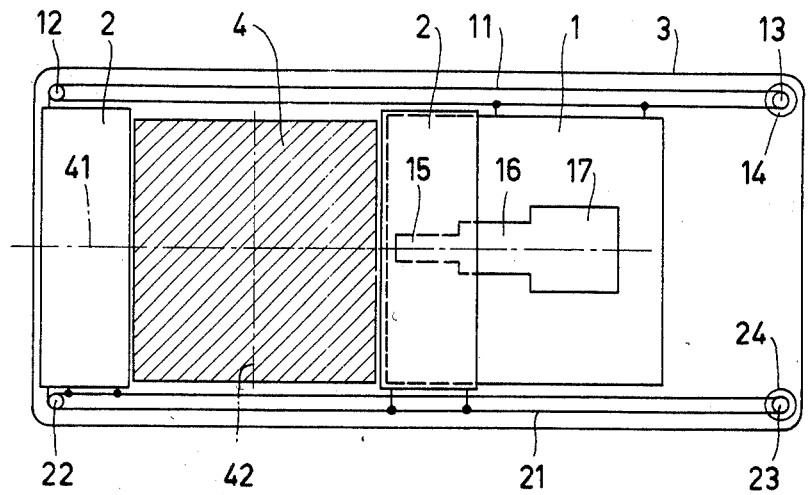
FIG. 1 is a schematic illustration of a diaphragm arrangement according to the invention.

The diaphragm means shown in FIG. 1 comprise a first diaphragm plate 1 (height-limiting) and a diaphragm assembly (width-limiting) consisting of two rectangular diaphragm plates 2. The diaphragm means screens stray radiation from the film surfaces not to be exposed, and defines the boundaries of an exposure field by imaging its edges on the film. Therefore, in the spot-film device 3 (shown schematically), the diaphragms are located in planes parallel to each other immediately in front of the film (not shown).

Reference numeral 4 designates the exposure field. This field is the surface in the film plane on which the radiation beam is incident. The maximum possible exposure field, for example 35×35 cm, is shown in the drawing. The horizontal center line of the exposure field is designated by reference numeral 41 and the vertical center line is designated by reference numeral 42. The smaller exposure fields which can be produced with the diaphragm are also symmetrical to the center lines 41 and 42.

The distance between the facing vertically extending longitudinal sides of the two rectangular diaphragm plates 2 determines the width of the exposure field. The diaphragm plates 2, arranged symmetrically with respect to the vertical center line 42, are connected to a toothed belt 21. Belt 21 is passed across rollers 22 and 23, which are secured to the lefthand lower side and to the righthand lower side, respectively, of the spot-film device Roller 23 can be driven by a motor 24.

The lefthand diaphragm plate 2 is connected to the part of the toothed belt 21 extending above the rollers, while the righthand diaphragm plate 2 is connected to the part of the toothed belt 21 below the rollers 22 and 23. As a result, the diaphragm plates 2 are moved horizontally in opposite directions. Plates 2 are moved but invariably over the same distance, toward each other when the roller 23 is driven by the motor 24 in clockwise direction. They are moved away from each other when roller 23 is driven counterclockwise.

The diaphragm 1, like the diaphragm plates 2, preferably consists of lead. Plate 1 is connected to a toothed belt 11, which is passed across rollers 12 and 13 secured to the spot-film device. The roller 13 is driven by a motor 14. In this manner, the diaphragm 1 can be displaced in the horizontal direction.

The diaphragm 1 has three rectangular sections 15, 16 and 17, which are arranged symmetrically with respect to the horizontal center line 41. The rectangular sections join each other directly so that there is no strap between them. The section 17 has a height of, for example, 12 cm. That is, the horizontal diaphragm plates limiting section 17 each extend a distance of 6 cm from the horizontal center line 41. Section 17 has a width of, for example, 15 cm. The section 16 has a height of 9 cm and a width of 12 cm, while the section 15 has a height of about 4.5 cm and a width also of about 12 cm.

The edges of the sections 15, 16 and 17 consequently have the form of a staircase ascending in clockwise direction above the center line 41 and descending in the same direction below the center line 41. In the drawing, the three sections are limited on both sides by the material of the plate, but essentially the plate could be open on the left hand or the righthand side.

If the width of the exposure is to be adjusted, the motor 24 is merely switched on and the plates 2 are moved into the radiation path until the desired width is obtained. If, moreover, the height of the exposure is to be adjusted, the diaphragm 1 is also moved into the radiation path until the center of the section of the desired height coincides with the vertical center line 42. The diaphragm plates 2 are then moved toward each other so that the width of the field limited by them is not larger than the width of the corresponding section of diaphragm 1. However, the diaphragm plates 2 may also be moved still further toward each other.

If, for example, a film format of 24×30 cm horizontal (the term "horizontal" means that the longer side extends in horizontal direction) should be subdivided four times (twice in the direction of height and twice in the direction of width), the diaphragm 1 is moved in a counterclockwise direction until the center of the section 17 coincides with the vertical center line 42. The diaphragm plates 2 are moved toward each other over such a distance that their distance is about 15 cm.

If instead a format of 24×24 cm should be subdivided four times, the diaphragm 1 is moved into the same position, but the diaphragm plates 2 are moved closer toward each other because the width of the exposure field must become smaller.

It appears from this example that the width of a section 17 is not determinative of the diaphragm aperture. The width of a section must therefore be chosen so that it is larger than or as large as the maximum width of the format of the exposure (in the example chosen about 15 cm). If the width is chosen to be larger, the requirements imposed on the accuracy of positioning the diaphragm 1 become less stringent. However, as a result, the occupied space and the weight of the diaphragm 1 become larger.

If an exposure of 18×24 cm horizontal should be subdivided four times, the diaphragm 1 is moved in counterclockwise direction until the center of the section 16 coincides with the vertical center line 42. The diaphragms 2 are moved toward each other in a corresponding manner. With Colon exposures, in which the format of 18×24 cm horizontal should be subdivided eight times (twice in the direction of width and four times in the direction of height), the section 15 is moved toward the center line 42.

It is advantageous that subdivisions of different heights are possible without it being necessary to exchange a plate or a cone, which in fact is not possible in given examination methods.

Figure 2:
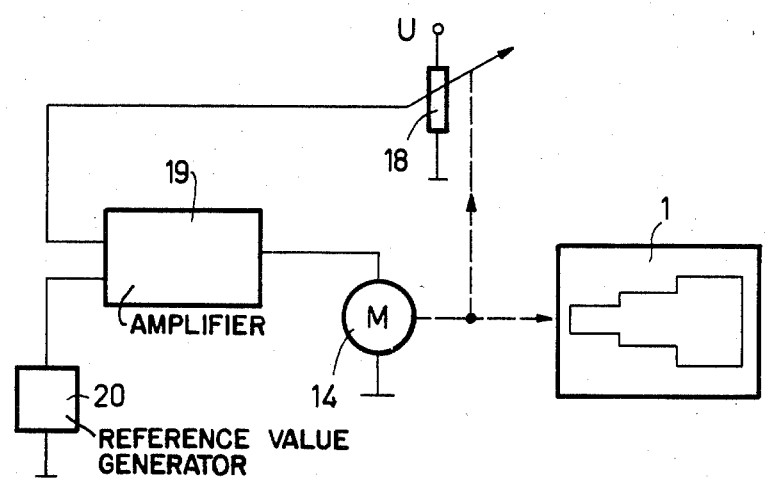
FIG. 2 is a schematic diagram of means for controlling the positioning of each of the two diaphragm assemblies according to the invention.

FIG. 2 schematically shows a control circuit for the motor 14, which moves the diaphragm 1. The motor 14, which according to FIG. 1 moves the diaphragm 1 in the horizontal direction via a toothed belt 11, at the same time displaces the tap of a potentiometer 18. The tap is coupled with, for example, the roller 13. The potentiometer is connected to a voltage U. The voltage at the tap of the potentiometer 18 is therefore a measure of the instantaneous position of the diaphragm 1.

In a control amplifier 19, the voltage at the tap of the potentiometer 18, which corresponds to the actual position value, is compared with a reference position value. The reference is supplied by a reference value generator 20 in the form of a direct voltage. The reference value generator 20 may be a suitable resistance voltage divider. Essentially, however, the reference value may also be supplied by a microprocessor through a digital-to-analogue converter. The motor 24 is controlled correspondingly, as is known per se from U.S. Pat. No. 3,875,411 (corresponding to German Offenlegungsschrift No. 2248101).

What is claimed is:

1. A diaphragm arrangement for an X-ray spot film device, said diaphragm arrangement comprising:
    a first diaphragm having a first axis and having at least two rectangular apertures therein along the axis, said first diaphragm being displaceable in the direction of its axis, each rectangular aperture having a different size;
    a second diaphragm having a second axis transverse to the first axis, said second diaphragm defining an aperture having edges parallel to the second axis, said second diaphragm being arranged to overlap the first diaphragm so that the two diaphragms selectively define an exposure field wherein said first diaphragm defines a dimension in the direction of said second axis and said second diaphragm defines a dimension in the direction of said first axis; and
    motor means for displacing the first diaphragm along said first axis.

2. A diaphragm arrangement as claimed in claim 1, characterized in that the second diaphragm comprises two diaphragm plates having edges parallel to the second axis which face each other, said plates being displaceable in the direction of the first axis, said plates being coupled to each other so that their edges are always symmetrical about the second axis.

3. A diaphragm arrangement as claimed in claim 2, characterized in that the rectangular apertures in the first diaphragm adjoin each other.

4. A diaphragm arrangement as claimed in claim 3, characterized in that the first axis is horizontal and the second axis is vertical.

5. A diaphragm arrangement as claimed in claim 4, characterized in that each aperture in the first diaphragm has a horizontal dimension equal to the maximum width of the exposure field.

6. A diaphragm arrangement as claimed in claim 1, characterized in that the rectangular apertures in the first diaphragm adjoin each other.

7. A diaphragm arrangement as claimed in claim 6, characterized in that the first axis is horizontal and the second axis is vertical.

8. A diaphragm arrangement as claimed in claim 7, characterized in that each aperture in the first diaphragm has a horizontal dimension equal to the maximum width of the exposure field.

9. A diaphragm arrangement as claimed in claim 1, characterized in that the first axis is horizontal, and the second axis is vertical.

10. A diaphragm arrangement as claimed in claim 9, characterized in that each aperture in the first diaphragm has a horizontal dimension equal to the maximum width of the exposure field.

11. A diaphragm arrangement as claimed in claim 10, characterized in that the motor means also displaces the two diaphragm plates of the second diaphragm.

* * * * *